United States Patent [19]

Gesser et al.

[11] Patent Number: 4,618,732
[45] Date of Patent: Oct. 21, 1986

[54] DIRECT CONVERSION OF NATURAL GAS TO METHANOL BY CONTROLLED OXIDATION

[76] Inventors: Hyman D. Gesser, 218 Girton Ave., Winnipeg, Manitoba; Norman R. Hunter, Lot 68, Red River Drive, R.M. of Ritchot, Manitoba; Lawrence Morton, 1018-110 Adamar Road, Winnipeg, Manitoba, all of Canada

[21] Appl. No.: 735,983

[22] Filed: May 20, 1985

[51] Int. Cl.$^4$ ............................................. C07C 29/48
[52] U.S. Cl. ................................. 568/910.5; 422/208; 568/910
[58] Field of Search .............................. 568/910.5, 910

[56] References Cited

U.S. PATENT DOCUMENTS

| | | | |
|---|---|---|---|
| 1,976,790 | 10/1934 | Lewis et al. | 568/910.5 |
| 2,004,714 | 6/1935 | Thompson et al. | 568/910.5 |
| 2,042,134 | 5/1936 | Walker | 568/910.5 |
| 2,128,909 | 9/1938 | Bludworth | 568/910.5 |
| 3,092,667 | 6/1963 | Murphy | 568/910 |
| 4,243,613 | 6/1981 | Brockhaus et al. | 568/482 |

FOREIGN PATENT DOCUMENTS

| | | |
|---|---|---|
| 291411 | 7/1929 | Canada . |
| 300567 | 5/1930 | Canada . |
| 394823 | 2/1941 | Canada . |
| 1096884 | 3/1981 | Canada .............................. 260/573.9 |

OTHER PUBLICATIONS

Perry et al., "Perry's Chemical Engineers Handbook", 4th ed., 1963, 21-3 and 21-4.
The Direct Conversion of Methane to Methanol—Proceedings of the VI International Symposium on Alcohol Fuels Technology, Ottawa, Canada, May 21-25, 1984.

Primary Examiner—J. E. Evans

[57] ABSTRACT

A process of directly converting natural gas to methanol employs controlled oxidation. The reaction takes place in an inert reactor, i.e. one having internal surfaces which do not affect the reaction, in the absence of a catalyst. The natural gas is intimately mixed with air or oxygen prior to introduction of the mixed gases into the reactor. Reaction takes place at an elevated temperature of 300° to 500° C. and at an elevated pressure of 10 to 100 atmospheres. The percentage of oxygen in the mixture of reactant gases is kept below 20% by volume and is preferably 2 to 10% by volume. Apparatus for carrying out the method is also provided.

13 Claims, 7 Drawing Figures

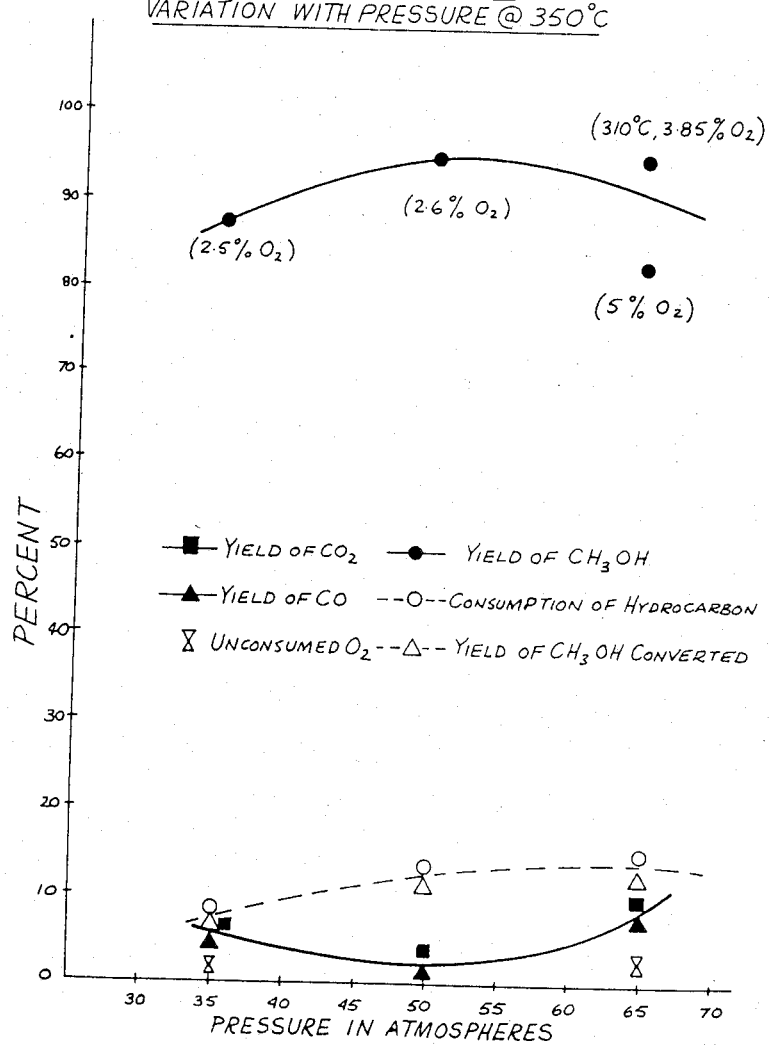

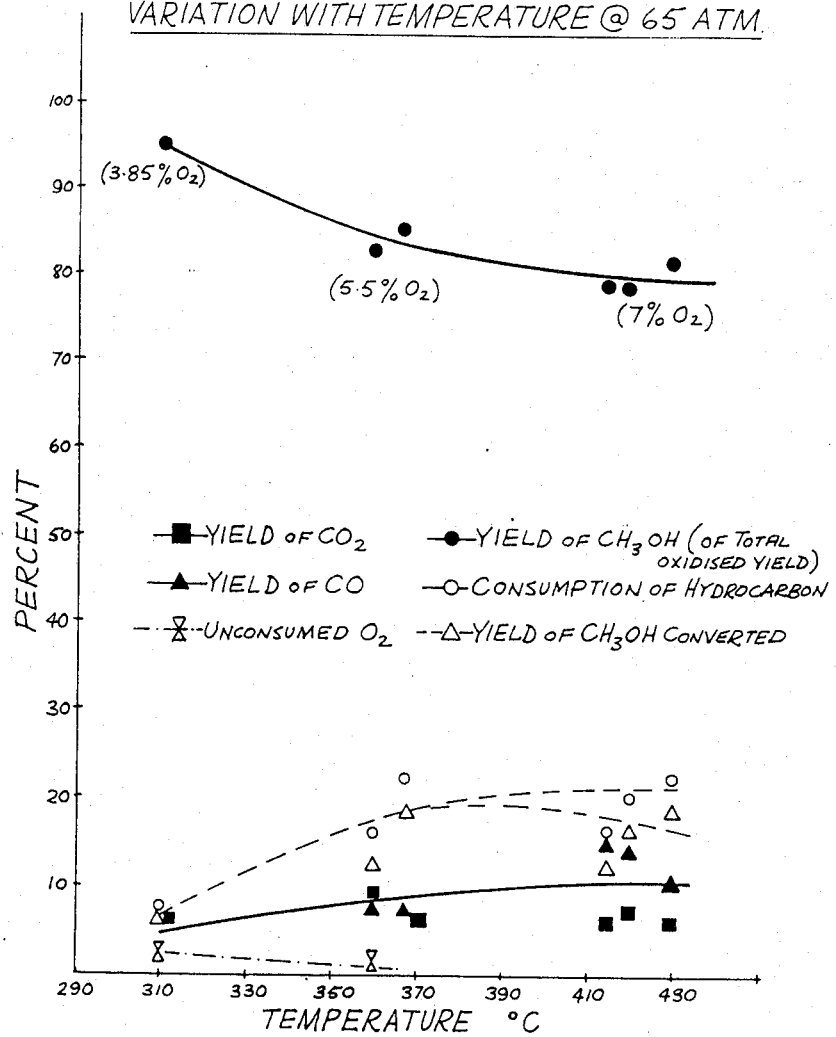

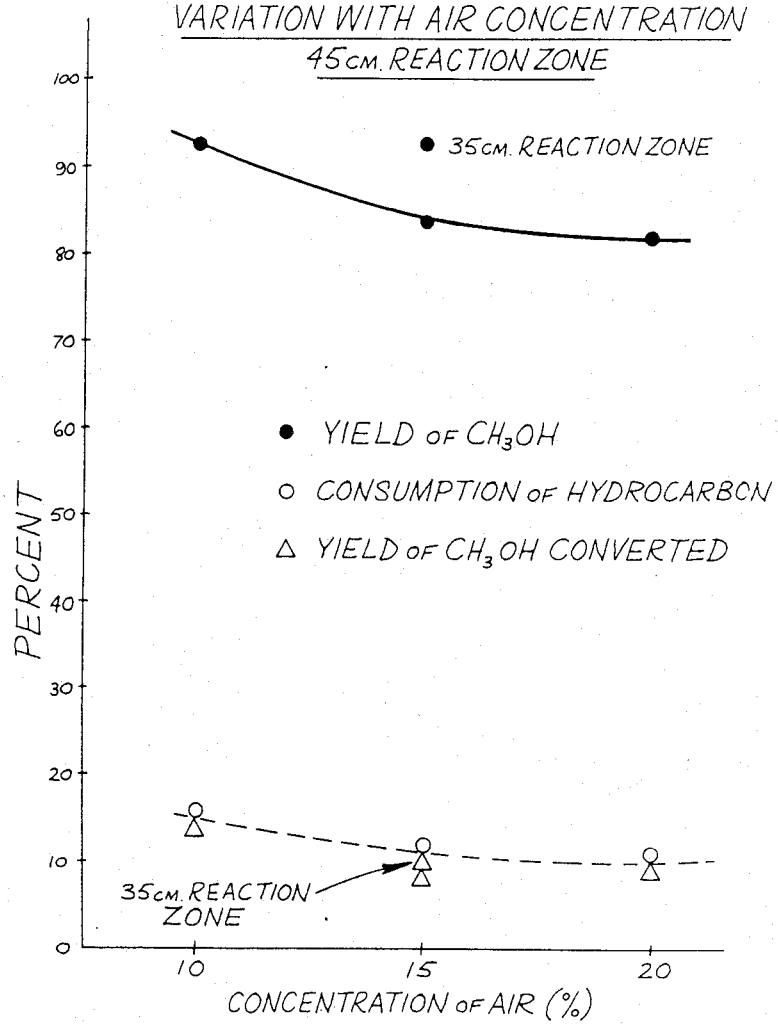

DIRECT CONVERSION OF NATURAL GAS TO METHANOL BY CONTROLLED OXIDATION

BACKGROUND OF THE INVENTION

I. Field of the Invention

This invention relates to the controlled oxidation of natural gas to produce primarily methanol with little or no formaldehyde.

II. Description of the Prior Art

Reserves of natural gas in Canada and often in other hydrocarbon-producing countries are quite high although direct utilization of the gas as a power source is inconvenient for reasons of storage, handling and application. Conversion to a liquid fuel would obviate the problems of storage and handling. The most suitable liquid fuel obtainable from natural gas (or more generally from methane which is the main component of natural gas) is methanol which can be used as a direct substitute for gasoline. This conversion can be achieved by the controlled oxidation of methane to methanol, i.e. oxidation under conditions such that further oxidation to higher oxidation state products is limited.

The conventional procedure for the conversion of natural gas to methanol first of all involves a reaction with water to produce synthesis gas, which is a mixture of carbon monoxide and hydrogen, followed by catalytic conversion of the synthesis gas to methanol or other substances.

Since both reactions, i.e. the conversion of natural gas to synthesis gas and the subsequent conversion of synthesis gas to methanol require the presence of a catalyst, high purity gases must be employed and large plants must be constructed in order to achieve an economy of scale. Poisoning of the catalysts invariable occurs and the catalysts must often be replaced or regenerated.

The direct conversion of methane or natural gas to methanol has been attempted in the past, but the conversion yields have not been very high and selectivity for methanol has been low. Moreover, catalysts are also generally employed for such reactions, leading to the problems outlined above. For example, E. H. Boomer in Canadian Patent No. 291,411 issued on Jul. 16, 1929 stressed the need for a variety of catalysts to effect the reaction.

Bone and Newitt in Canadian Patent No. 394,823 issued on Feb. 25, 1941 describe a partial oxidation of gaseous hydrocarbons, but a high proportion of the product is formaldehyde as well as some methanol. Catalysts were also suggested for this reaction.

More recently, Brockhaus and Franke in Canadian Patent No. 1,096,884 issued on Mar. 3, 1981 have described a method of converting methane to methanol and formaldehyde using a flame reactor. The system gives very poor yields and ratios of methanol to formaldehyde which vary from 1 to 4:1, which is quite low.

Accordingly, an object of the invention is to provide a process for the direct conversion of natural gas to methanol which is relatively easy to operate and gives a good yield of methanol with high selectivity.

Another object of the invention is to provide an apparatus for carrying out the above process.

SUMMARY OF THE INVENTION

In one aspect, the invention provides a process for the direct conversion of natural gas to methanol. This is achieved by reacting natural gas with oxygen or air in the absence of a catalyst in an inert reactor at an elevated temperature and pressure. To obtain a high yield of methanol, the reactant gases, i.e. natural gas and oxygen or air, are first intimately mixed.

In another aspect, the invention provides apparatus for carrying out a method of converting natural gas to methanol. The apparatus comprises an inert reactor and means for intimately mixing the oxygen or air and natural gas prior to their introduction into the reactor. Means are also provided to ensure that the gases reach a suitable elevated temperature and pressure in the reactor.

By the term "inert reactor" we mean a reactor that has internal surfaces made of, or coated with, a material which has no substantial adverse effect upon the methanol yields or selectivity. Preferably, the reactor is made of stainless steel lined with glass or polytetrafluoroethylene (e.g. as sold under the trade mark Teflon). Alternatively, the internal surfaces of the reactor may be coated with non-reactive waxes or salts. However, the use of a glass-lined reactor is particularly preferred in the present invention.

It is to be noted that the invention makes no use of a catalyst and, indeed, requires the above-noted step of employing an inert reactor to make sure that materials on the internal reactor surfaces do not affect the reaction.

The avoidance of the use of a catalyst not only circumvents the problems of the prior art mentioned above but, quite unexpectedly, results in a high selectivity for methanol and a good yield. For example, the ratio of methanol to formaldehyde achievable with the present invention can be as high as 10,000:1 or more.

An advantage of the present invention, at least in its preferred forms, is that it can make feasible the economic conversion of natural gas from relatively small gas fields into a storable fuel (methanol) without the need to produce a very large plant. At present, many small gas fields are either being capped or flared, resulting in large amounts of natural gas being lost to the energy pool. When the present invention is employed at fairly low pressures (e.g. 10 atm.) it is possible to convert natural gas into methanol as the natural gas leaves the wellhead and before it enters the pipeline, thus making vehicle fuel available in remote communities.

Other objects, features and advantages of the present invention will be apparent from the more detailed discussion of the invention which follows.

DESCRIPTION OF THE DRAWINGS

FIG. 5 is a graph showing the yield of methanol from natural gas when the reaction of the invention is carried out at various pressures;

FIG. 6 is a graph showing the yield of methanol from natural gas when the method of the invention is carried out at various temperatures; and FIG. 7 shows the yield of methanol from natural gas when the reaction of the invention is carried out with various percentages of air in the reacting gases.

DETAILED DESCRIPTION OF THE INVENTION AND THE PREFERRED EMBODIMENTS

Figure 1:
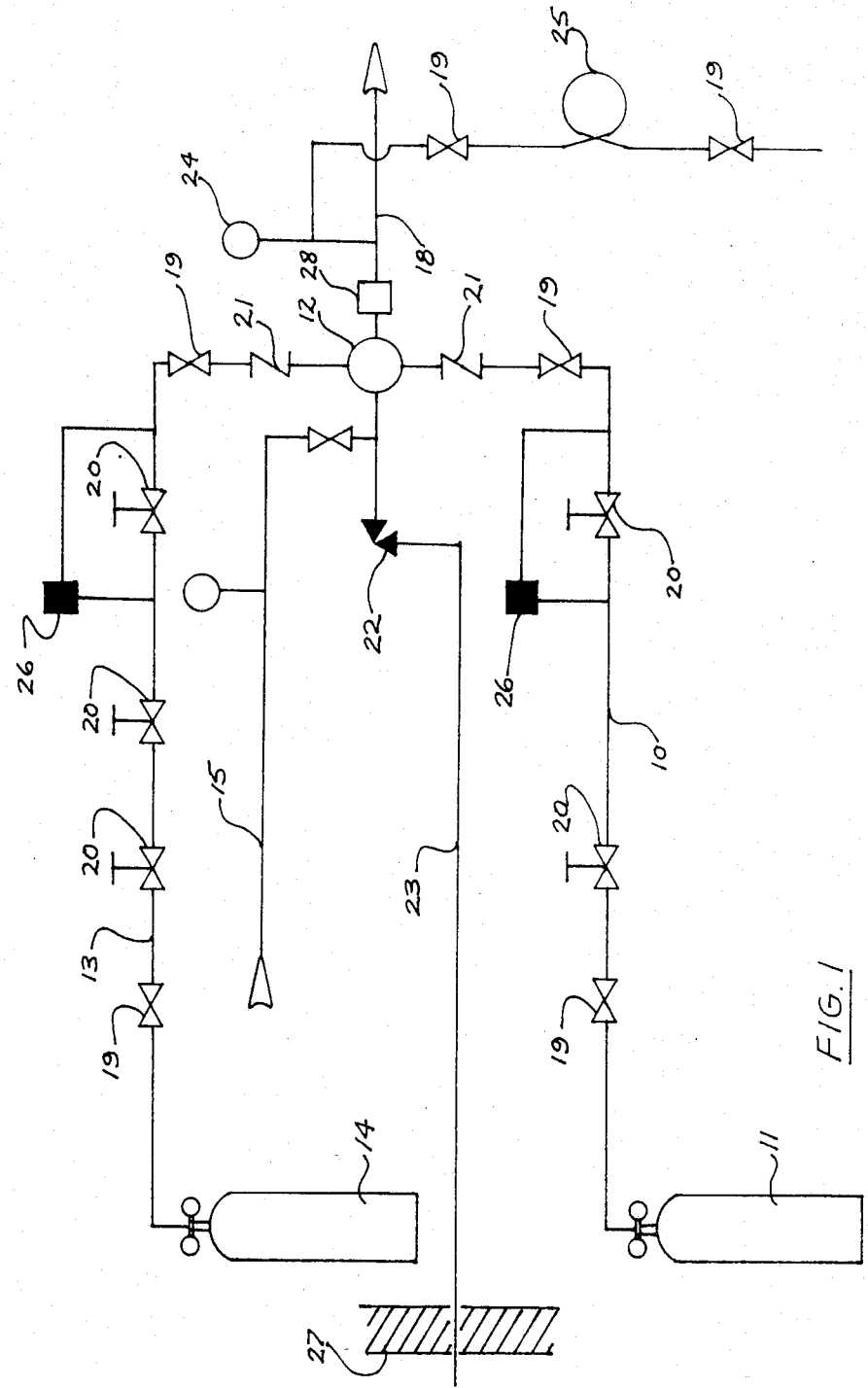
FIG. 1 is a schematic representation of one embodiment of an apparatus for carrying out the method of the present invention.

The present invention preferably relates to a dual flow system, i.e. a system in which the natural gas and the oxygen or air are kept separate until mixed just prior to being introduced into the reactor. However, the invention can also be used, if desired, with a single flow system in which the oxygen or air and natural gas are mixed and stored together prior to the reaction. The single flow system has the disadvantage that it is not suited to a continuous-operation and also that it produces a risk of fire or explosion (although the gases can be mixed in ratios outside the explosive range).

When carrying out a dual flow system, the inventors have found that the gases must undergo intimate and thorough mixture before they are introduced into the reaction zone.

The mixing of gases preferably takes place in a pre-mixing chamber or "cross" of relatively small volume and then pass through a short pre-reactor section before entering the heated reaction zone. However, when mixing gases at high pressure in a relatively small volume, laminar flow often takes place with the oxygen or air forming a narrow homogeneous stream within the general flow of natural gas. The oxygen or air has little chance of becoming dispersed throughout the reaction stream prior to reaching the reaction zone. Without wishing to be bound by theory, when this takes place it is postulated that the natural gas is oxidized initially to methanol which is further oxidized, at the periphery of the oxygen stream, i.e. in an oxygen-rich environment, to higher oxidation products.

Accordingly, it is necessary to intimately mix the natural gas and oxygen or air and this should be done to the greatest extent possible. However, it has been found that methods commonly employed for breaking up laminar flow, such as passing gases through stainless steel wool or capillary tubing can adversely affect the reaction. This is because such methods can affect the progress of the reaction and can even cause the mixture to ingite. To overcome this, in a preferred form of the invention, the reaction gases are first separately passed through discs of porous polyethylene as the gases are introduced into the premixing chamber and then passed through a porous mass of inert material, such as turnings of polytetrafluoroethylene, packed within the premixing chamber. The degree of mixing can be further improved, by locating a vernier needle valve (e.g. a commercial valve sold under the name Aerosmith V54-2-11) in the flow line between the premixing chamber and the reactor. This measure considerably improves the degree of mixing of the gases and results in a high yield of and selectivity for methanol. The optimum setting of the needle valve is when the vernier has been turned one 360° turn out from the fully closed position. With this setting, it has been found in practice that the mixing of the reactant gases approaches 100% (homogeneity) before the gases enter the reactor.

As noted above, the reaction is influenced by the nature of the reactor wall. High methanol yields can be obtained when the walls of the reactor are inert, for example when made of or coated with glass (e.g. heat resistant glass as sold under the trade mark Pyrex) and polytetrafluoroethylene (for example Teflon). It would therefore seem that the controlled oxidation of natural gas to methanol takes place almost entirely in the gas phase and when an inert reactor is employed the methanol specific yield can be as high as 85 to 95% of the hydrocarbon consumed (at sub 10% oxygen concentrations).

The pressures employed in the reactor are generally in the range of 10 to 100 atmospheres, more preferably 10 to 60 atmospheres, and even more preferably 10 to 50 atmospheres.

The temperature employed in the reactor is generally in the range of 300° to 500° C., more preferably 350° to 450° C.

The amount of oxygen in the oxygen/methane mixture should preferably be in the range of 2 to 20% by volume, more preferably 2 to 10%, and even more preferably 2 to 5%. The use of air instead of oxygen does not affect the reaction, so it can be concluded that the nitrogen present in air does not interfere with the methanol yield or conversion of the natural gas and that the oxygen concentration is the dominant factor.

Incidentally, the amount of oxygen should preferably not exceed 20% by volume of the total gases in order to ensure that the gases remain outside the explosion range. The relative amounts of natural gas and oxygen or air may be controlled, for example, by flow control valves.

The contact time of the gases depends to some extent on the temperature, pressure and relative oxygen concentration, but the normal contact time is within the range of 2 to 1000 seconds, preferably 5 to 15 seconds, and more preferably about 10 seconds.

It has been found that the temperature of the exit line for the gases and reactants leaving the reactor has an effect on the methanol yield. It is believed that some decomposition of the newly formed methanol may take place either in the gas phase or on the tubing walls in the exit line and that this decomposition can be reduced by maintaining the temperature in the exit line below about 200° C. However, the temperature should not be so low that the reaction products condense in the exit line. A suitable temperature (e.g. 180°–200° C.) can usually be obtained by insulating but not heating the exit line.

The products of the reaction include unreacted methane, some ethane and propane present in natural gas, methanol, carbon monoxide, carbon dioxide and water. This mixture of products is treated to remove the methanol and the unreacted hydrocarbons which are then either recirculated into the reactor for further reaction or sent to a second reactor serially attached to the first reactor. The length and diameter of the reactor tube are not critical and can be chosen to give the desired residence time of the reacting gases. Diameters of 0.5 to 2.5 cm (internal diameter) are common. However, in large scale industrial equipment different reactor sizes may be employed.

As indicated previously, by employing the method of the present invention, as much as 90% of the methane consumed can be converted into methanol and as much as 10 to 20% of the methane can be reacted in each pass through the reactor.

An apparatus for carrying out the process of the invention, is shown in FIG. 1 of the drawings and is described in detail below.

FIG. 1 shows, in simplified form, apparatus for mixing oxygen and natural gas prior to their introduction into a reactor (dual flow system) where they are converted to methanol and other reaction products. The apparatus comprises a high pressure line 10 for conveying natural gas at a fixed rate from the cylinder 11 to a small pre-mixing chamber 12. A high pressure line 13 likewise conveys oxygen or air from a cylinder 14 to the premixing chamber 12.

Nitrogen from a suitable source (not shown) may also be conveyed to the pre-mixing chamber 12 via a line 15. The nitrogen can be used to purge the apparatus, for pressure testing and it may act as an internal standard for later analysis of the reaction products by gas chromatography.

Figure 3:
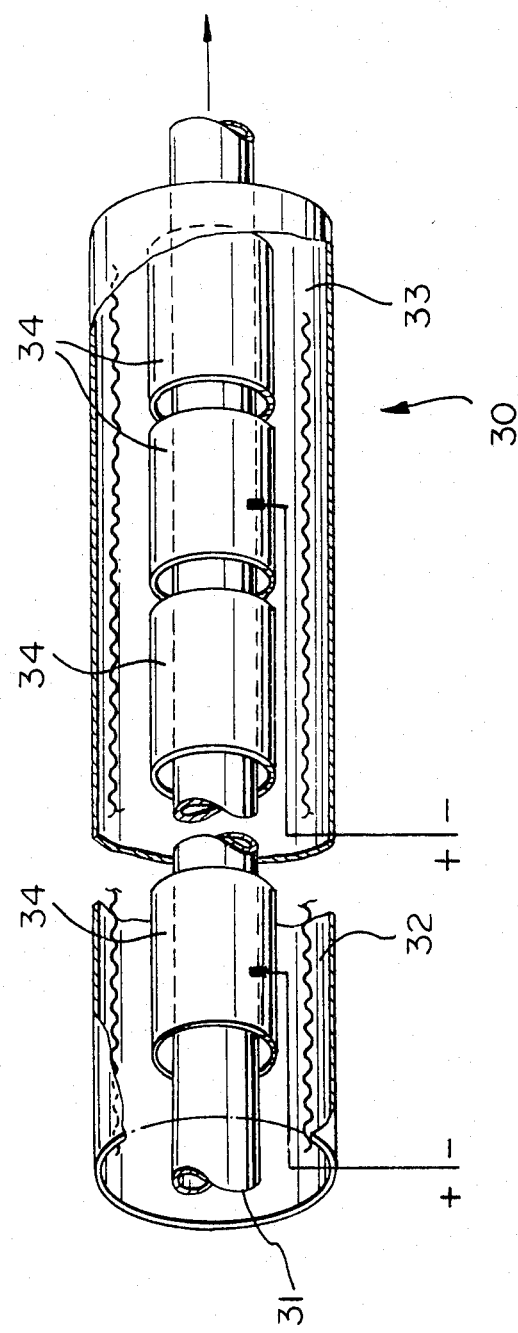
FIG. 3 is a representation on an enlarged scale of a reactor which may be employed with the apparatus as shown in FIG. 1.

The natural gas and oxygen or air are intimately and thoroughly mixed in the pre-mixing chamber 12 and are then conveyed via a line 18 through a needle valve 28 to a reactor (not shown in FIG. 1, but see FIG. 3).

In addition to the above, the apparatus comprises valves 19, metering valves 20, check valves 21, a relief valve 22 vented to the exterior through a wall 27 via pipe 23, a pressure gauge 24 for measuring the reaction pressure (this is preferably a Heiss-Bourdon gauge), a reactant sampling loop 25 and flow transducers 26. It is believed that the purpose of this additional equipment will be self-evident to a person skilled in this art.

Figure 2:
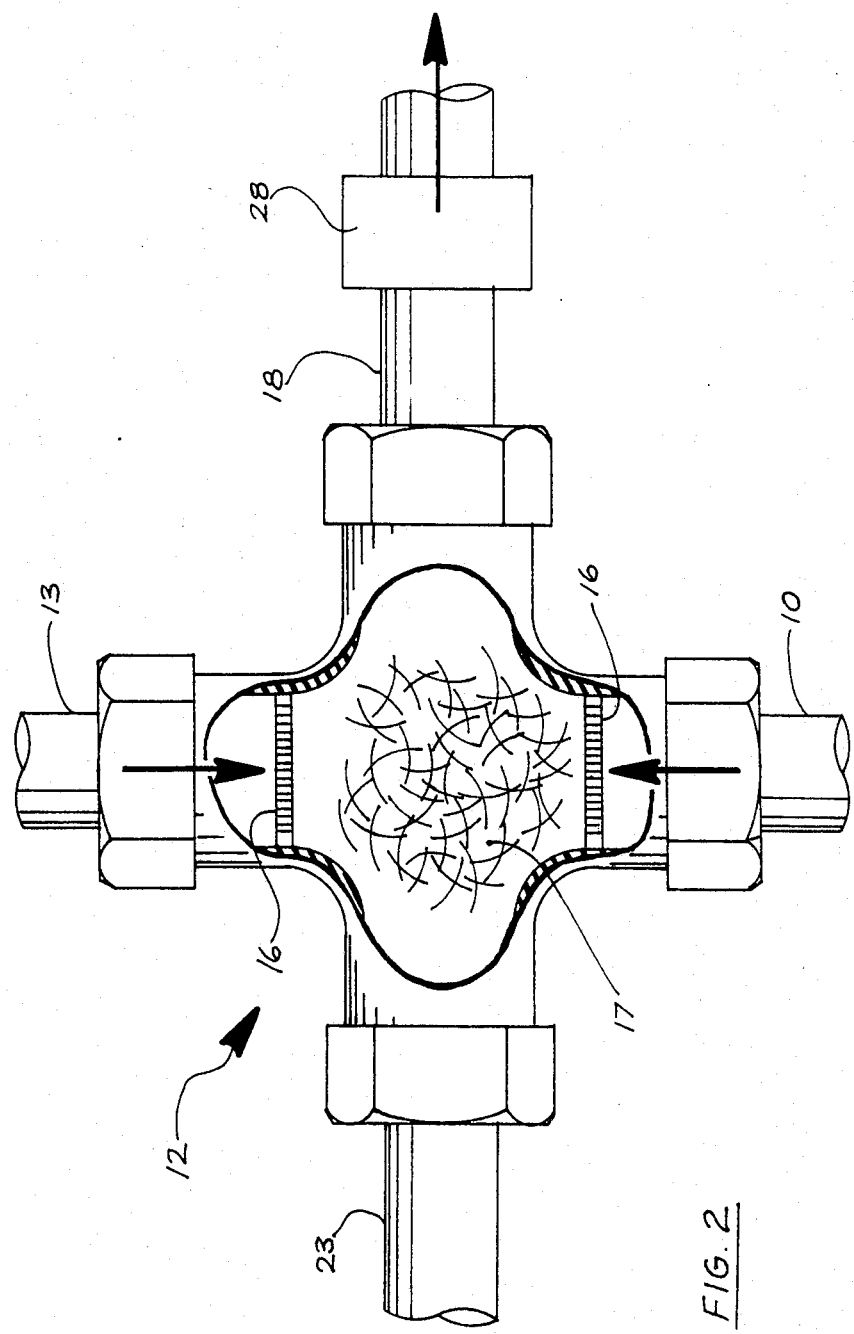
FIG. 2 is a cross section on an enlarged scale of a premixing chamber employed in the apparatus of FIG. 1.

The premixing chamber 12 is shown in more detail in FIG. 2 of the drawings. Its volume is kept small to minimize the damage should the gas mixture ignite or explode. Intimate and thorough mixing of the gases is achieved in the premixing chamber 12 by first passing the gases through diffusers 16 which are porous disks of inert material having pores small enough to achieve good diffusion of the gases while allowing a satisfactory gas flow. Advantageously, the porous disks are plastic frits made of polyethylene.

The interior of the premixing chamber 12 is packed with a porous inert mass 17, e.g. turnings of polytetrafluoroethylene (e.g. as sold under the trade mark Teflon). The diffusers 16 diffuse the gases to cause intermingling and the porous mass 17 prevents laminar flow of the gases and the resulting turbulent flow improves the mixing effect. If desired, however, a magnetic stirrer (not shown) may be used instead of the porous mass 17.

The mixed gases then pass to the reactor through the line 18 via the needle valve 28. The needle valve further improves the mixing of the gases and may result in a completely homogeneous gas mixture.

A suitable reactor 30 is as shown in FIG. 3 of the drawings.

It comprises a stainless steel tube 31 lined with glass or polytetrafluoroethylene to render the inner surfaces inert to the reaction. The reaction tube 31 is heated over the majority of its length (which may be, for example, 45 cm) by two tube heaters 32 and 33. The first tube heater 32 may be, for example, a 400 watt variac controlled heater heating a 10 cm length of the reactor tube 31. The second tube heater 33 may be, for example, a 800 watt heater heating the remaining 35 cm of the reactor tube 31. The temperature may be monitored by thermocouples and controlled to within ±5° C. Aluminum spacers 34 are located between the tube heaters 32, 33 and the reactor tube 31.

Figure 4:
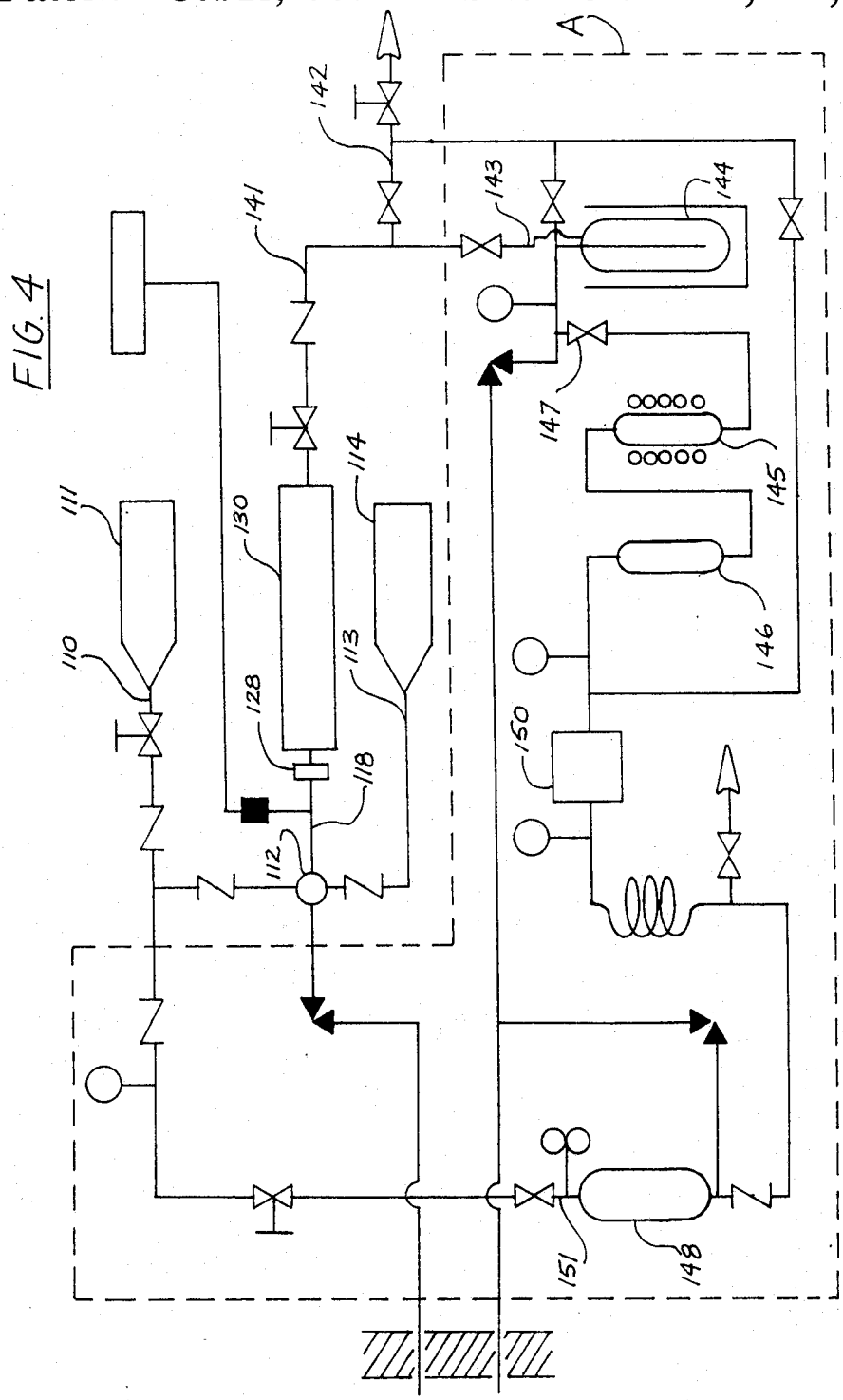
FIG. 4 is a schematic representation of an alternative embodiment for carrying out the method of the present invention.

FIG. 4 shows an alternative apparatus for carrying out the method of the invention. This alternative apparatus has many parts in common with the apparatus shown in FIG. 1 and these are identified by the same reference numerals as used in FIG. 1 except that the prefix "1" is additionally provided.

Natural gas is fed through a line 110 from a suitable source 111 to a premixing chamber 112. Likewise, oxygen or air is fed through a line 113 from a source 114 to the premixing chamber 112. The gases are mixed in the chamber 112 and fed through a pipe 118 to a reactor 130 via a needle valve 128 which completes the intimate and thorough mixing of the gases.

The reaction products exiting the reactor through line 141 may be sampled through line 142 for gas chromatographic analysis. However, the bulk of the products are supplied to separation and recycling equipment identified by the box A in FIG. 4. Thus, the products pass through a line 143 to a condenser 144 for the removal of the methanol product. Once the pressure of the gas in the condenser builds up to a suitable level (for example 150 to 200 psig.), the gas may be admitted to the carbon monoxide and carbon dioxide scrubbers 145 and 146 by opening valve 147. The gas then enters a recycle gas storage cylinder 148 by passing through one way check valves (not shown) in the head of a gas booster. The pressure is allowed to build up in this way (e.g. to around 300 psig) to the point where back pressure, in the recycle line, causes the reactor pressure to increase. Once the pressure reaches a predetermined value (e.g. 450 psig.) the gas is admitted through line 151 to the premixing chamber 112. However, the recycled gas is first mixed with incoming natural gas from the supply 111. In this way, unreacted methane is continuously recycled to the reactor 130 to give a high yield of methanol.

Using apparatus of the above type, various tests and experiments were carried out, as explained in the following Examples.

EXAMPLE 1

Natural gas was reacted with oxygen in equipment of the type shown in FIG. 1 employing a reactor with inert internal walls.

A variety of reactions was carried out varying the reaction pressure, the reaction temperature and the percentage of oxygen in the reaction mixture.

The results, giving the percentage yield of methanol per amount of $CH_4$ reacted and the percentage consumption of hydrocarbon, are shown in FIGS. 5, 6 and 7 of the accompanying drawings. Other results, such as yield of $CO_2$ and CO and unconsumed $O_2$ are also shown.

FIG. 5 shows the yields for reactions carried out at pressures varying from 35 to 65 atm. at a temperature of 350° C. The optimum yield of methanol (over 90%) was obtained at 50 atm. and the highest consumption of hydrocarbon (15%) was at 65 atm.

FIG. 6 shows the yield of methanol and consumption of hydrocarbon for reactions carried out at a pressure of 65 atm. at a variety of reaction temperatures from 310° to 430° C. The highest yield of methanol (over 90%) was obtained at 310° C. and the highest consumption of hydrocarbon (over 20%) was obtained at 370° C.

FIG. 7 shows the yield of methanol and consumption of hydrocarbon for reactions carried out with varying concentrations of air at fixed temperature and pressure. The maximum yield of methanol and the highest consumption of hydrocarbon was obtained at 10% by volume of air in the reactant gases.

EXAMPLE 2

Using apparatus of the type shown in FIG. 1, similar reactions were carried out with a glass-lined reactor and a polytetrafluoroethylene-lined reactor. The results are shown in Table 1 below.

TABLE 1

Oxidation of Natural Gas

| Reactor | % Oxygen | % CH$_3$OH Yield | % CH$_4$ Consumed |
|---|---|---|---|
| Glass | 5.5 | 92 | 13 |
| Polytetrafluoroethylene | 4.9 | 91 | 11 |

Thus, in this experiment, a glass-lined reactor gave the better results.

EXAMPLE 3

In this example, the effect of the thoroughness with which the reactant gases are mixed on the methanol field was tested.

A premixing chamber of the type shown in FIG. 2 was employed except that the various means to enhance mixing were varied as shown in Table 2.

TABLE 2

| Premixing Chamber | Needle Valve | % O$_2$ | % Yield CH$_3$OH |
|---|---|---|---|
| No diffusers 16 or porous mass 17 | No | 5-10 | 8.5 |
| No diffusers 16 steel wool used as porous mass 17 | No | 10 | 33.6 |
| Diffusers 16 Teflon turnings as porous mass 17 | Yes | 7 | 57 |

EXAMPLE 4

A series of tests was carried out using reactors having internal surfaces comprising glass, silver, copper, polytetrafluoroethylene and stainless steel at temperatures around 350° C., at a pressure of 30 atm., a flow rate of 10 seconds (reactor volume)$^{-1}$, and an oxygen concentration of about 5% by volume.

The results are shown in Table 3.

TABLE 3

| Reactor Surface | % CH$_3$OH | % Hydrocarbon Conversion |
|---|---|---|
| glass (pyrex) | 92.07 | 13.36 |
| silver | 48.52 | 5.97 |
| copper | 11.11 | 0.72 |
| polytetrafluoroethylene (Teflon) | 91.11 | 10.79 |
| stainless steel | 74.10 | 4.76 |

As can be seen from the Table, glass and polytetrafluoroethylene gave excellent results, with glass giving the best results.

Preferred embodiments of the invention have been described above and it will be apparent to persons skilled in the art that modifications and variations are possible. All such modifications and variations form part of the present invention insofar as they do not depart from the spirit and scope of the appendant claims.

We claim:

1. A process for converting natural gas containing methane to methanol, comprising:

thoroughly and intimately mixing natural gas with gaseous air or oxygen to achieve substantially complete homogeneity of these gases;

feeding the resulting gas mixture to an inert reactor under elevated pressure, said inert reactor having an internal surface surrounding a zone in which said gases react, said surface being made of a material selected from the group consisting of glass, non-reactive plastics, non-reactive waxes and non-reactive salts; and reacting said gases in said reaction zone at an elevated temperature in the absence in said reaction zone of any added material which measurably affects the rate of selectivity of the reaction or the yield of the product.

2. A process according to claim 1 wherein said thorough and intimate mixing is achieved by separately passing said gases at said elevated pressure into a mixing chamber containing a porous mass through porous diffuser plates and then feeding the resulting gas mixture to said inert reactor.

3. A process according to claim 2 wherein said gases are fed to said reactor via a needle valve to effect further intimate mixing of the gases.

4. A process according to claim 1 wherein said surface is made of glass.

5. A process according to claim 1 wherein said surface is made of polytetrafluoroethylene.

6. A process according to claim 1 wherein said reation is carried out at a temperature in the range of 300°-400° C.

7. A process according to claim 1 wherein said reaction is carried out at a pressure in the range of 10 to 100 atmospheres.

8. A process according to claim 1 wherein said gases are reacted in said reactor for a time period in the range of 2 to 1000 seconds.

9. A process according to claim 1 wherein respective amounts of said natural gas and air or oxygen are mixed together to give an oxygen content in the resulting mixed gas in the range of 2 to 20%.

10. A process according to claim 1 wherein methanol is removed from a reaction product resulting from reacting said gases, and any unreacted methane in said reaction product is further subjected to the mixing, feeding and reacting step as defined in claim 1.

11. A process according to claim 10 wherein said unreacted methane undergoes said further reacting step by recirculating it to the reactor used for the initial reaction of natural gas with gaseous air or oxygen.

12. A process according to claim 1 wherein said gases are each raised to said elevated pressure before said thorough and intimate mixing step takes place.

13. A process according to claim 1 wherein the natural gas and oxygen or air are introduced into the reactor in the absence of other gaseous materials.

* * * * *